US012406758B2

(12) United States Patent
Oda et al.

(10) Patent No.: US 12,406,758 B2
(45) Date of Patent: Sep. 2, 2025

(54) TRANSPORT SYSTEM, TRANSPORT METHOD, AND PROGRAM

(71) Applicant: TOYOTA JIDOSHA KABUSHIKI KAISHA, Toyota (JP)

(72) Inventors: Shiro Oda, Anjo (JP); Tetsuya Taira, Nagakute (JP); Satoshi Toyoshima, Okazaki (JP); Yuta Watanabe, Toyota (JP); Takeshi Matsui, Nisshin (JP); Takayoshi Nasu, Okazaki (JP); Kei Yoshikawa, Nagoya (JP); Yusuke Ota, Nagakute (JP); Yutaro Ishida, Toyota (JP); Yuji Onuma, Nagoya (JP); Kyosuke Arai, Toyota (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 817 days.

(21) Appl. No.: 17/505,014

(22) Filed: Oct. 19, 2021

(65) Prior Publication Data
US 2022/0208328 A1 Jun. 30, 2022

(30) Foreign Application Priority Data
Dec. 24, 2020 (JP) .................. 2020-215100

(51) Int. Cl.
*G16H 20/13* (2018.01)
*B25J 11/00* (2006.01)
(Continued)

(52) U.S. Cl.
CPC ............ *G16H 20/13* (2018.01); *B25J 11/009* (2013.01); *G16H 10/60* (2018.01); *G16H 20/10* (2018.01); *G16H 40/20* (2018.01); *G05D 1/00* (2013.01)

(58) Field of Classification Search
CPC ........ G16H 20/13; G16H 10/60; G16H 40/20; G16H 20/10; B25J 11/009; B25J 5/007; B25J 11/00
See application file for complete search history.

(56) References Cited

U.S. PATENT DOCUMENTS

| 2003/0014222 A1* | 1/2003 | Klass | ............. G16H 10/20 702/190 |
| 2018/0121864 A1* | 5/2018 | Sullivan | ............. B65G 63/002 |

(Continued)

FOREIGN PATENT DOCUMENTS

| CN | 109636188 A | * | 4/2019 | ............. B25J 11/008 |
| CN | 111145860 A | * | 5/2020 | ............. G16H 20/10 |

(Continued)

OTHER PUBLICATIONS

CN 111145860, "A In-patient Medicine Distributing Method, System, and Storage Medium", Li, et al. (Year: 2020).*

(Continued)

*Primary Examiner* — Ernesto A Suarez
*Assistant Examiner* — Laurence R Brothers
(74) *Attorney, Agent, or Firm* — Dinsmore & Shohl LLP

(57) ABSTRACT

A transport system is a transport system for transporting a transported object using a mobile robot that is autonomously moveable. The mobile robot transports a plurality of the transported objects. The transport system detects that a transport destination of the transported object is different from a receiving location. The transport system outputs that there is the transported object of a different transport destination to a recipient who is present at the receiving location.

15 Claims, 7 Drawing Sheets

(51) Int. Cl.
    *G05D 1/00*        (2024.01)
    *G16H 10/60*      (2018.01)
    *G16H 20/10*      (2018.01)
    *G16H 40/20*      (2018.01)
    *B25J 5/00*        (2006.01)

(56) References Cited

U.S. PATENT DOCUMENTS

2019/0205819 A1    7/2019    Igata et al.
2019/0306663 A1*  10/2019   Ruth .................. G06Q 10/0833

FOREIGN PATENT DOCUMENTS

| DE | 19711228 C1 * | 9/1998 | ........... B65G 1/0485 |
|---|---|---|---|
| JP | 2019-119537 A | 7/2019 | |
| KR | 20190109338 A * | 9/2019 | ........... G05D 1/0221 |

OTHER PUBLICATIONS

DE 19711228, "Distribution Depot for Goods on Palettes", Danielowsky, et al. (Year: 1998).*
CN-109636188-A (Year: 2019).*
KR-20190109338-A (Year: 2019).*
CN-111145860-A (Year: 2020).*

* cited by examiner

FIG. 2
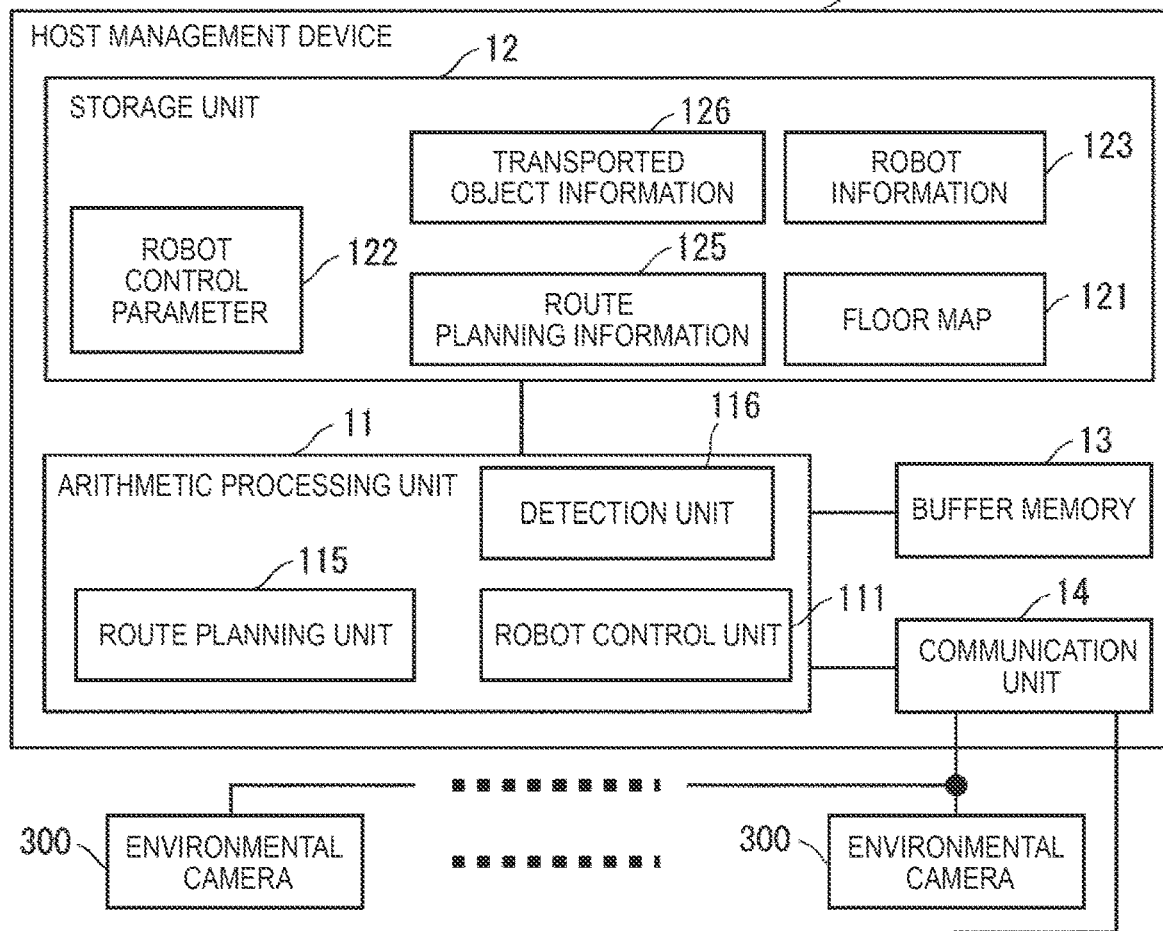
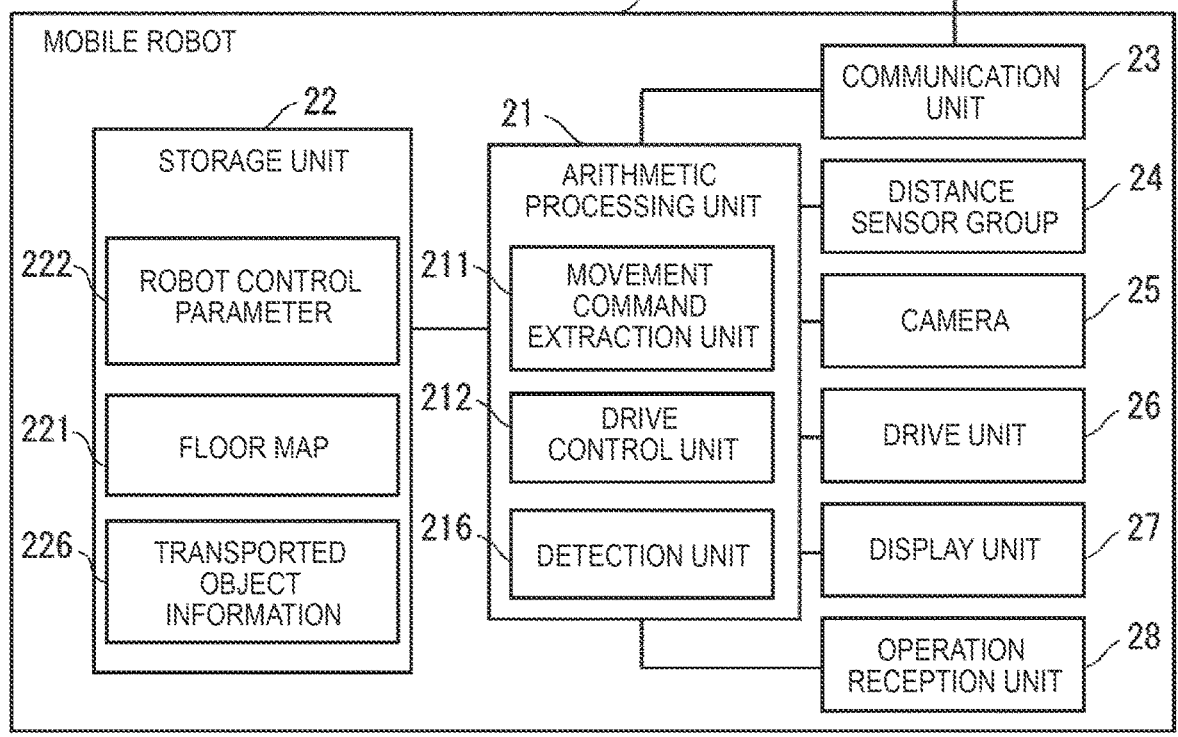

FIG. 4

| TRANSPORTED OBJECT | CONTENT | TRANSPORT SOURCE | TRANSPORT DESTINATION | PLANNED USER | ROBOT ID | STATUS |
|---|---|---|---|---|---|---|
| 001 | MEDICINE | S001 | G001 | U001 | AAA | TRANSPORT UNDER WAY |
| 002 | MEDICINE | S001 | G002 | U002 | AAA | TRANSPORT UNDER WAY |
| 003 | EQUIPMENT | S002 | G003 | U003 | BBB | POST-TRANSPORT |
| 004 | SPECIMEN | S003 | G004 | U004 | CCC | PRE-TRANSPORT |
| ... | ... | ... | ... | ... | ... | ... |

TRANSPORT SYSTEM, TRANSPORT METHOD, AND PROGRAM

CROSS-REFERENCE TO RELATED APPLICATION

This application claims priority to Japanese Patent Application No. 2020-215100 filed on Dec. 24, 2020, incorporated herein by reference in its entirety.

BACKGROUND

1. Technical Field

The present disclosure relates to transport systems, transport methods, and programs.

2. Description of Related Art

Japanese Unexamined Patent Application Publication No. 2019-119537 (JP 2019-119537 A) discloses a transport system for transporting luggage. In JP 2019-119537 A, an autonomous mobile body has a luggage storage that can be electrically locked and unlocked. When a client stores the luggage in the luggage storage, the luggage storage is locked. When the autonomous mobile body moves to a receiving location, the recipient unlocks the luggage storage.

SUMMARY

In such a transport system, it is desired to appropriately transport the luggage (also referred to as a transported object). Further, loading and transporting a plurality of transported objects by the autonomous mobile body (also referred to as a mobile robot) enables more efficient transport. However, when the mobile robot transports a plurality of transported objects of different transport destinations, there is an issue that the recipient mistakenly receives the luggage.

The present disclosure has been made to solve such an issue, and provides a transport system, a transport method, and a program capable of appropriately transporting a transported object.

A transport system according to the present embodiment is a transport system for transporting a transported object using a mobile robot that is autonomously moveable. The mobile robot transports a plurality of the transported objects. The transport system detects that a transport destination of the transported object is different from a receiving location. The transport system outputs that there is the transported object of a different transport destination to a recipient who is present at the receiving location.

The above transport system may detect, when information on a location movement of a patient is input to an electronic medical record system that stores patient information, that the transport destination is different from the receiving location based on the information on the location movement.

The above transport system may detect that the transport destination is different from the receiving location based on an IC tag attached to the transported object.

In the above transport system, when the transport system acquires an estimated dispensing time for completing dispensing of medicine that is the transported object, the mobile robot may go to pick up the medicine according to the estimated dispensing time.

In the above transport system, upon detecting that the transport destination is different from the receiving location, the transport system may transport the transported object to a correct transport destination.

A transport method according to the present embodiment is a transport method for transporting a transported object using a mobile robot that is autonomously moveable. The transport method includes: transporting a plurality of the transported objects by the mobile robot; detecting that a transport destination of the transported object is different from a receiving location; and outputting that there is the transported object of a different transport destination to a recipient who is present at the receiving location.

The above transport method may include detecting, when information on a location movement of a patient is input to an electronic medical record system that stores patient information, that the transport destination is different from the receiving location based on the information on the location movement.

The above transport method may include detecting that the transport destination is different from the receiving location based on an IC tag attached to the transported object.

The above transport method may include going to pick up medicine according to an estimated dispensing time by the mobile robot, when the estimated dispensing time for completing dispensing of the medicine that is the transported object is acquired.

The above transport method may include transporting the transported object to a correct transport destination upon detecting that the transport destination is different from the receiving location.

A program according to the present embodiment is a program that causes a computer to execute a transport method for transporting a transported object using a mobile robot that is autonomously moveable. The transport method includes: transporting a plurality of the transported objects by the mobile robot; detecting that a transport destination of the transported object is different from a receiving location; and outputting that there is the transported object of a different transport destination to a recipient who is present at the receiving location.

The above program may detect, when information on a location movement of a patient is input to an electronic medical record system that stores patient information, that the transport destination is different from the receiving location based on the information on the location movement.

The above program may detect that the transport destination is different from the receiving location based on an IC tag attached to the transported object.

In the above program, when an estimated dispensing time for completing dispensing of medicine that is the transported object is acquired, the mobile robot may go to pick up the medicine at the estimated dispensing time.

In the above program, upon detecting that the transport destination is different from the receiving location, the program may transport the transported object to a correct transport destination.

The present disclosure can provide a transport system, a transport method, and a program capable of appropriately transporting a transported object.

BRIEF DESCRIPTION OF THE DRAWINGS

Features, advantages, and technical and industrial significance of exemplary embodiments of the disclosure will be described below with reference to the accompanying drawings, in which like signs denote like elements, and wherein:

FIG. 2 is a control block diagram of a transport system according to the present embodiment;

FIG. 4 is a table showing transported object information;

DETAILED DESCRIPTION OF EMBODIMENTS

Hereinafter, the present disclosure will be described through embodiments of the disclosure, but the disclosure according to the scope of the claims is not limited to the following embodiments. Moreover, not all of the configurations described in the embodiments are indispensable for solving the problem.

Schematic Configuration

Figure 1:
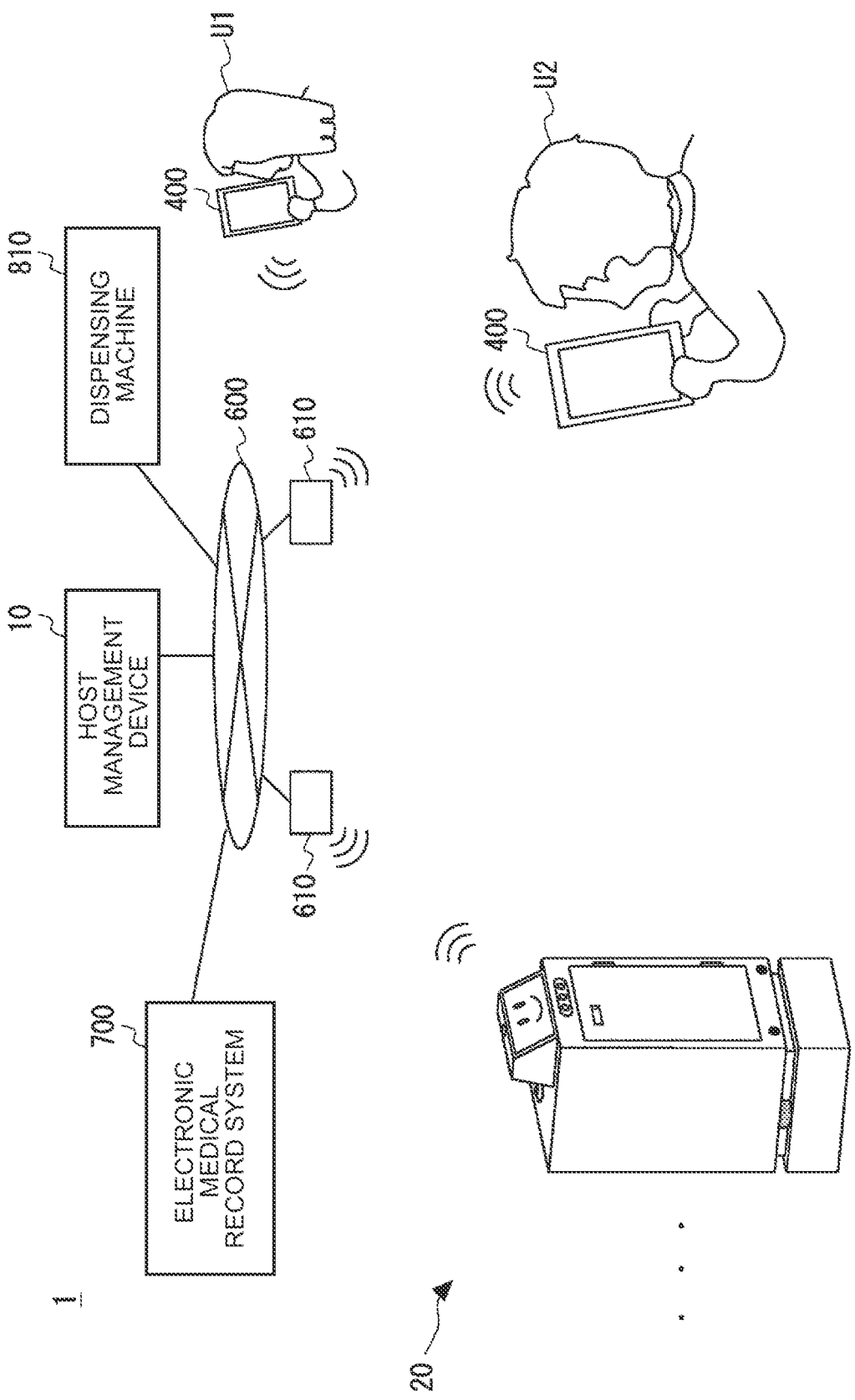
FIG. 1 is a conceptual diagram illustrating an overall configuration of a system in which a mobile robot according to the present embodiment is used.

FIG. 1 is a conceptual diagram illustrating an overall configuration of a system 1 in which a mobile robot 20 according to the present embodiment is used. For example, the mobile robot 20 is a transport robot that executes transport of a transported object as a task. The mobile robot 20 autonomously travels in order to transport a transported object in a medical welfare facility such as a hospital, a rehabilitation center, a nursing facility, and an elderly care facility. The system 1 according to the present embodiment can also be used in a commercial facility such as a shopping mall.

A user U1 stores the transported object in the mobile robot 20 and requests the transport. The mobile robot 20 autonomously moves to the set destination to transport the transported object. That is, the mobile robot 20 executes a luggage transport task (hereinafter also simply referred to as a task). In the following description, the location where the transported object is loaded is referred to as a transport source, and the location where the transported object is delivered is referred to as a transport destination.

For example, it is assumed that the mobile robot 20 moves in a general hospital having a plurality of clinical departments. The mobile robot 20 transports equipment, consumables, medical equipment, and the like between the plurality of clinical departments. For example, the mobile robot 20 delivers the transported object from a nurse station of one clinical department to a nurse station of another clinical department. Alternatively, the mobile robot 20 delivers the transported object from the storage of the equipment and the medical equipment to the nurse station of the clinical department. The mobile robot 20 also delivers medicine dispensed in the dispensing department to the clinical department or a patient that is scheduled to use the medicine.

Examples of the transported object include medicines, consumables such as packaging bags, specimens, testing instruments, medical equipment, hospital food, and equipment such as stationery. The medical equipment includes sphygmomanometers, blood transfusion pumps, syringe pumps, foot pumps, nurse call devices, bed leaving sensors, low-pressure continuous inhalers, electrocardiogram monitors, drug injection controllers, enteral nutrition pumps, artificial respirators, cuff pressure gauges, touch sensors, aspirators, nebulizers, pulse oximeters, artificial resuscitators, aseptic devices, echo machines, and the like. Meals such as hospital food and inspection meals may also be transported. Further, the mobile robot 20 may transport used equipment, tableware that have been used during meals, and the like. When the transport destination is on a different floor, the mobile robot 20 may move using an elevator or the like.

The system 1 includes the mobile robot 20, a host management device 10, a network 600, a communication unit 610, and a user terminal 400. The user U1 or a user U2 can make a transport request for the transported object using the user terminal 400. For example, the user terminal 400 is a tablet computer, a smartphone, or the like. The user terminal 400 only needs to be an information processing device capable of wireless or wired communication.

In the present embodiment, the mobile robot 20 and the user terminal 400 are connected to the host management device 10 via the network 600. The mobile robot 20 and the user terminal 400 are connected to the network 600 via the communication unit 610. The network 600 is a wired or wireless local area network (LAN) or wide area network (WAN). The host management device 10 is connected to the network 600 by wire or wirelessly. The communication unit 610 is, for example, a wireless LAN unit installed in each environment. The communication unit 610 may be a general-purpose communication device such as a WiFi router.

Various signals transmitted from the user terminals 400 of the users U1 and U2 are once sent to the host management device 10 via the network 600, and transmitted from the host management device 10 to the target mobile robots 20. Similarly, various signals transmitted from the mobile robot 20 are once sent to the host management device 10 via the network 600, and are transmitted from the host management device 10 to the target user terminal 400. The host management device 10 is a server connected to each equipment, and collects data from each equipment. The host management device 10 is not limited to a physically single device, and may have a plurality of devices that perform distributed processing. Further, the host management device 10 may be distributedly provided in edge devices such as the mobile robot 20. For example, a part or all of the system 1 may be installed in the mobile robot 20.

The user terminal 400 and the mobile robot 20 may transmit and receive signals without passing through the host management device 10. For example, the user terminal 400 and the mobile robot 20 may directly transmit and receive signals by wireless communication. Alternatively, the user terminal 400 and the mobile robot 20 may transmit and receive signals via the communication unit 610.

The user U1 or the user U2 requests the transport of the transported object by using the user terminal 400. Hereinafter, description is made assuming that the user U1 is the transport requester at the transport source and the user U2 is the planned recipient at the transport destination (destination). Needless to say, the user U2 at the transport destination can also make a transport request. Further, a user who is located at a location other than the transport source or the transport destination may make a transport request.

When the user U1 makes a transport request, the user U1 inputs, using the user terminal 400, the content of the transported object, the receiving point of the transported object (hereinafter also referred to as the transport source), the delivery destination of the transported object (hereinafter also referred to as the transport destination), the estimated arrival time at the transport source (the receiving time of the transported object), the estimated arrival time at the transport destination (the transport deadline), and the like. Hereinafter, these types of information are also referred to as transport request information. The user U1 can input the transport request information by operating the touch panel of the user terminal 400. The transport source may be a location where the user U1 is present, or a storage location for the transported object. The transport destination is a location where the user U2 or a patient who is scheduled to use the transported object is present.

The user terminal 400 transmits the transport request information input by the user U1 to the host management device 10. The host management device 10 is a management system that manages a plurality of mobile robots 20. The host management device 10 transmits an operation command for executing a transport task to the mobile robot 20. The host management device 10 determines the mobile robot 20 that executes the transport task for each transport request. Then, the host management device 10 transmits a control signal including an operation command to the mobile robot 20. The mobile robot 20 moves from the transport source so as to arrive at the transport destination in accordance with the operation command.

For example, the host management device 10 assigns a transport task to the mobile robot 20 at or near the transport source. Alternatively, the host management device 10 assigns a transport task to the mobile robot 20 heading toward the transport source or its vicinity. The mobile robot 20 to which the task is assigned goes to the transport source to pick up the transported object. The transport source is, for example, a location where the user U1 who requested the task is present.

When the mobile robot 20 arrives at the transport source, the user U1 or another staff member loads the transported object on the mobile robot 20. The mobile robot 20 on which the transported object is loaded autonomously moves with the transport destination set as the destination. The host management device 10 transmits a signal to the user terminal 400 of the user U2 at the transport destination. Thus, the user U2 can know that the transported object is being transported and the estimated arrival time. When the mobile robot 20 arrives at the set transport destination, the user U2 can receive the transported object stored in the mobile robot 20. In this way, the mobile robot 20 executes the transport task.

In the overall configuration described above, each element of the control system can be distributed to the mobile robot 20, the user terminal 400, and the host management device 10 to construct the control system as a whole. Further, it is possible to collect substantial elements for realizing the transport of the transported object in a single device to construct the transport system. The host management device 10 controls one or more mobile robots 20.

Further, the host management device 10 is linked with an electronic medical record system 700 and a dispensing machine 810. The electronic medical record system 700 stores information on patients (also referred to as patient information). For example, when a medical worker such as a doctor or a nurse inputs the patient information using the user terminal 400, the patient information is stored in a memory of the electronic medical record system 700 or the like. Further, the medical worker can view and update the patient information stored in the electronic medical record system 700 through the user terminal 400.

The dispensing machine 810 is a device for dispensing medicine to be administered to a patient. The dispensing machine 810 is a device or a robot that measures, packages, or sorts the medicine. For example, a pharmacist operates the dispensing machine 810 to dispense the prescribed medicine. The medicine dispensed by the dispensing machine 810 is considered as the transported object. The host management device 10, the electronic medical record system 700, and the dispensing machine 810 are accessible to each other.

Control Block Diagram

FIG. 2 shows a control block diagram showing a control system of the system 1. As shown in FIG. 2, the system 1 includes the host management device 10, the mobile robot 20, and environmental cameras 300.

The system 1 efficiently controls a plurality of mobile robots 20 while causing the mobile robots 20 to autonomously move in a predetermined facility. Therefore, a plurality of environmental cameras 300 are installed in the facility. For example, the environmental camera 300 is installed in a passage, a hallway, an elevator, an entrance/exit, etc. in the facility.

The environmental cameras 300 acquire images of ranges in which the mobile robot 20 moves. In the system 1, the host management device 10 collects the images acquired by the environmental cameras 300 and the information based on the images. Alternatively, the images or the like acquired by the environmental cameras 300 may be directly transmitted to the mobile robots. The environmental cameras 300 may be surveillance cameras or the like provided in a passage or an entrance/exit in the facility. The environmental cameras 300 may be used to determine the distribution of congestion status in the facility.

In the system 1 according to the present embodiment, the host management device 10 performs route planning based on the transport request information. The host management device 10 instructs a destination for each mobile robot 20 based on route planning information created by the host management device 10. Then, the mobile robot 20 autonomously moves toward the destination designated by the host management device 10. The mobile robot 20 autonomously moves toward the destination using sensors, floor maps, position information, and the like provided in the mobile robot 20 itself.

For example, the mobile robot 20 travels so as not to come into contact with surrounding equipment, objects, walls, and people (hereinafter collectively referred to as peripheral objects). Specifically, the mobile robot 20 detects the distance from the peripheral object and travels while keeping a distance from the peripheral object by a certain distance (defined as a distance threshold value) or more. When the distance from the peripheral object becomes equal to or less than the distance threshold value, the mobile robot 20 decelerates or stops. In this way, the mobile robot 20 can travel without coming into contact with peripheral objects. Since contact can be avoided, safe and efficient transport is possible.

The host management device 10 includes an arithmetic processing unit 11, a storage unit 12, a buffer memory 13, and a communication unit 14. The arithmetic processing unit 11 performs arithmetic for controlling and managing the mobile robot 20. The arithmetic processing unit 11 can be implemented as a device capable of executing a program such as a central processing unit (CPU) of a computer, for example. Various functions can also be realized by a program. Only a robot control unit 111, a route planning unit 115, and a detection unit 116, which are characteristics of the arithmetic processing unit 11, are shown in FIG. 2, but other processing blocks can also be provided.

The robot control unit 111 performs arithmetic for remotely controlling the mobile robot 20 and generates a control signal. The robot control unit 111 generates a control signal based on route planning information 125 and the like, which will be described later. Further, the robot control unit 111 generates a control signal based on various types of information obtained from the environmental cameras 300 and the mobile robots 20. The control signal may include update information such as a floor map 121, robot information 123, and a robot control parameter 122, which will be described later. That is, when various types of information are updated, the robot control unit 111 generates a control signal according to the updated information.

The detection unit 116 detects that the transport destination of the transported object is different from the receiving location. The detection process of the detection unit 116 will be described later.

The route planning unit 115 performs route planning for each mobile robot 20. When the transport task is input, the route planning unit 115 performs route planning for transporting the transported object to the transport destination (destination) based on the transport request information. Specifically, the route planning unit 115 refers to the route planning information 125, the robot information 123, and the like already stored in the storage unit 12 to determine the mobile robot 20 that executes a new transport task. The starting point is the current position of the mobile robot 20, the transport destination of the immediately preceding transport task, the receiving point of the transported object, and the like. The destination is the transport destination of the transported object, a standby location, a charging location, or the like.

Here, the route planning unit 115 sets passing points from the starting point to the destination of the mobile robot 20. The route planning unit 115 sets the passing order of the passing points for each mobile robot 20. The passing points are set, for example, at branch points, intersections, lobbies in front of elevators, and their surroundings. In a narrow passage, it may be difficult for the mobile robots 20 to pass each other. In such a case, the passing point may be set at a location before the narrow passage. Candidates for the passing points may be registered in the floor map 121 in advance.

The route planning unit 115 determines the mobile robot 20 that performs each transport task from among the plurality of mobile robots 20 so that the task can be efficiently executed as the whole system. The route planning unit 115 preferentially assigns the transport task to the mobile robot 20 at standby or the mobile robot 20 located near the transport source.

The route planning unit 115 sets the passing points including a starting point and a destination for the mobile robot 20 to which the transport task is assigned. For example, when there are two or more movement routes from the transport source to the transport destination, the passing points are set so that the movement can be performed in a shorter time. Thus, the host management device 10 updates the information indicating the congestion status of the passages based on the images of the camera or the like. Specifically, locations where other mobile robots 20 are passing and locations where there are many people have a high degree of congestion. Therefore, the route planning unit 115 sets the passing points so as to avoid locations with a high degree of congestion.

The mobile robot 20 may be able to move to the destination by either a counterclockwise movement route or a clockwise movement route. In such a case, the route planning unit 115 sets the passing points so as to pass through the less congested movement route. The route planning unit 115 sets one or more passing points to the destination, so that the mobile robot 20 can move along a movement route that is not congested. For example, when a passage is divided at a branch point or an intersection, the route planning unit 115 sets a passing point at the branch point, the intersection, the corner, and the surroundings as appropriate. Thereby, the transport efficiency can be improved.

The route planning unit 115 may set the passing points in consideration of the congestion status of the elevator, the moving distance, and the like. Further, the host management device 10 may estimate the number of mobile robots 20 and the number of people at the estimated time when the mobile robot 20 passes through a certain location. Then, the route planning unit 115 may set the passing points in accordance with the estimated congestion status. Further, the route planning unit 115 may dynamically change the passing points in accordance with a change in the congestion status. The route planning unit 115 sets the passing points in order for the mobile robot 20 to which the transport task is assigned. The passing points may include the transport source and the transport destination. As will be described later, the mobile robot 20 autonomously moves so as to sequentially pass through the passing points set by the route planning unit 115.

The storage unit 12 is a storage unit that stores information necessary for managing and controlling the robot. In the example of FIG. 2, the floor map 121, the robot information 123, the robot control parameter 122, the route planning information 125, and transported object information 126 are shown, but the information stored in the storage unit 12 may include other information. The arithmetic processing unit 11 performs arithmetic using the information stored in the storage unit 12 when performing various processing. Further, various types of information stored in the storage unit 12 can be updated to the latest information.

The floor map 121 is map information of a facility in which the mobile robot 20 moves. The floor map 121 may be created in advance, may be generated from information obtained from the mobile robot 20, or may be information obtained by adding map correction information, which is generated from information obtained from the mobile robot 20, to a basic map created in advance.

The robot information 123 indicates the ID, model number, specifications, and the like of the mobile robot 20 managed by the host management device 10. The robot information 123 may include position information indicating the current position of the mobile robot 20. The robot information 123 may include information on whether the mobile robot 20 is executing a task or at standby. Further, the robot information 123 may include information indicating whether the mobile robot 20 is operating, out of order, or the like. Furthermore, the robot information 123 may include information on the transported object that can be transported and the transported object that cannot be transported.

The robot control parameter 122 indicates control parameters such as a threshold distance from a peripheral object for the mobile robot 20 managed by the host management device 10. The threshold distance is a margin distance for avoiding contact with the peripheral objects including a person. Further, the robot control parameter 122 may include information on the operating intensity such as the speed upper limit value of the moving speed of the mobile robot 20.

The robot control parameter 122 may be updated depending on the situation. The robot control parameter 122 may include information indicating the availability and usage status of the storage space of a storage 291. The robot control parameter 122 may include information on a transported object that can be transported and a transported object that cannot be transported. The robot control parameter 122 is associated with the above-described various types of information for each mobile robot 20.

The route planning information 125 includes the route planning information planned by the route planning unit 115. The route planning information 125 includes, for example, information indicating a transport task. The route planning information 125 may include the ID of the mobile robot 20 to which the task is assigned, the starting point, the content of the transported object, the transport destination, the transport source, the estimated arrival time at the transport destination, the estimated arrival time at the transport source, the arrival deadline, and the like. In the route planning information 125, the various types of information described above may be associated with each transport task. The route planning information 125 may include at least a part of the transport request information input from the user U1.

Further, the route planning information 125 may include information on the passing points for each mobile robot 20 and each transport task. For example, the route planning information 125 includes information indicating the passing order of the passing points for each mobile robot 20. The route planning information 125 may include the coordinates of each passing point on the floor map 121 and information on whether the mobile robot 20 has passed the passing point.

The transported object information 126 is information on the transported object for which the transport request has been made. For example, the transported object information 126 includes information such as the content (type) of the transported object, the transport source, and the transport destination. The transported object information 126 may include the ID of the mobile robot 20 in charge of the transport. Further, the transported object information 126 may include information indicating the status such as transport under way, pre-transport (before loading), and post-transport. The transported object information 126 is associated with these types of information for each transported object. The transported object information 126 will be described later.

The route planning unit 115 refers to various types of information stored in the storage unit 12 to formulate a route plan. For example, the route planning unit 115 determines the mobile robot 20 that executes the task, based on the floor map 121, the robot information 123, the robot control parameter 122, and the route planning information 125. Then, the route planning unit 115 refers to the floor map 121 and the like to set the passing points to the transport destination and the passing order thereof. Candidates for the passing points are registered in the floor map 121 in advance. The route planning unit 115 sets the passing points in accordance with the congestion status and the like. In the case of continuous processing of tasks, the route planning unit 115 may set the transport source and the transport destination as the passing points.

Two or more mobile robots 20 may be assigned to one transport task. For example, when the transported object is larger than the transportable capacity of the mobile robot 20, one transported object is divided into two and loaded on the two mobile robots 20. Alternatively, when the transported object is heavier than the transportable weight of the mobile robot 20, one transported object is divided into two and loaded on the two mobile robots 20. In this way, one transport task can be shared and executed by two or more mobile robots 20. It goes without saying that, when controlling mobile robots 20 of different sizes, route planning may be performed so that the mobile robot 20 capable of transporting the transported object receives the transported object.

Further, one mobile robot 20 may perform two or more transport tasks in parallel. For example, one mobile robot 20 may simultaneously load two or more transported objects and sequentially transport them to different transport destinations. Alternatively, while one mobile robot 20 is transporting one transported object, another transported object may be loaded on the mobile robot 20. Furthermore, the transport destinations of the transported objects loaded at different locations may be the same or different. In this way, the task can be executed efficiently.

In such a case, storage information indicating the usage status or the availability of the storage space of the mobile robot 20 may be updated. That is, the host management device 10 may manage the storage information indicating the availability and control the mobile robot 20. For example, the storage information is updated when the transported object is loaded or received. When the transport task is input, the host management device 10 refers to the storage information and directs the mobile robot 20 having room for loading the transported object to receive the transported object. In this way, one mobile robot 20 can execute a plurality of transport tasks at the same time, and two or more mobile robots 20 can share and execute the transport tasks. For example, a sensor may be installed in the storage space of the mobile robot 20 to detect the availability. Further, the capacity and weight of each transported object may be registered in advance.

The buffer memory 13 is a memory that stores intermediate information generated in the processing of the arithmetic processing unit 11. The communication unit 14 is a communication interface for communicating with a plurality of environmental cameras 300 and at least one mobile robot 20 provided in the facility where the system 1 is used. The communication unit 14 can perform both wired communication and wireless communication. For example, the communication unit 14 transmits a control signal necessary for controlling the mobile robot 20 to each mobile robot 20. The communication unit 14 receives the information collected by the mobile robot 20 and the environmental cameras 300.

The mobile robot 20 includes an arithmetic processing unit 21, a storage unit 22, a communication unit 23, a proximity sensor (for example, a distance sensor group 24), a camera 25, a drive unit 26, a display unit 27, and an operation reception unit 28. Although FIG. 2 shows only typical processing blocks provided in the mobile robot 20, the mobile robot 20 also includes many other processing blocks that are not shown.

The communication unit 23 is a communication interface for communicating with the communication unit 14 of the host management device 10. The communication unit 23 communicates with the communication unit 14 using, for example, a wireless signal. The distance sensor group 24 is, for example, a proximity sensor, and outputs proximity object distance information indicating a distance from an object or a person that is present around the mobile robot 20. The camera 25, for example, captures an image for grasping the surrounding situation of the mobile robot 20. The camera 25 can also capture an image of a position marker provided on the ceiling or the like of the facility, for example. The mobile robot 20 may be made to grasp the position of the mobile robot 20 itself by using this position marker.

The drive unit 26 drives drive wheels provided on the mobile robot 20. The drive unit 26 may include an encoder or the like that detects the number of rotations of the drive wheels and the drive motor thereof. The position of the mobile robot 20 (current position) may be estimated based on the output of the encoder. The mobile robot 20 detects its current position and transmits the information to the host management device 10.

The display unit 27 and the operation reception unit 28 are realized by a touch panel display. The display unit 27 displays a user interface screen that serves as the operation reception unit 28. Further, the display unit 27 may display information indicating the destination of the mobile robot 20 and the state of the mobile robot 20. The operation reception unit 28 receives an operation from the user. The operation reception unit 28 includes various switches provided on the mobile robot 20 in addition to the user interface screen displayed on the display unit 27.

The arithmetic processing unit 21 performs arithmetic used for controlling the mobile robot 20. The arithmetic processing unit 21 can be implemented as a device capable of executing a program such as a CPU of a computer, for example. Various functions can also be realized by a program. The arithmetic processing unit 21 includes a movement command extraction unit 211, a drive control unit 212, and a detection unit 216. Although FIG. 2 shows only typical processing blocks included in the arithmetic processing unit 21, the arithmetic processing unit 21 includes processing blocks that are not shown. The arithmetic processing unit 21 may search for a route between passing points.

The movement command extraction unit 211 extracts a movement command from the control signal given by the host management device 10. For example, the movement command includes information on the next passing point. For example, the control signal may include information on the coordinates of the passing points and the passing order of the passing points. The movement command extraction unit 211 extracts these types of information as a movement command.

Further, the movement command may include information indicating that the movement to the next passing point has become possible. When the passage width is narrow, the mobile robots 20 may not be able to pass each other. There are also cases where the passage cannot be used temporarily. In such a case, the control signal includes a command to stop the mobile robot 20 at a passing point before the location at which the mobile robot 20 should stop. After the other mobile robot 20 has passed or after the passage has become passable, the host management device 10 outputs a control signal informing the mobile robot 20 that the mobile robot 20 has become movable. Thus, the mobile robot 20 that has been temporarily stopped resumes movement.

The drive control unit 212 controls the drive unit 26 so that the drive unit 26 moves the mobile robot 20 based on the movement command given from the movement command extraction unit 211. For example, the drive unit 26 has drive wheels that rotate according to a control command value from the drive control unit 212. The movement command extraction unit 211 extracts the movement command so that the mobile robot 20 moves toward the passing point received from the host management device 10. The drive unit 26 rotationally drives the drive wheels. The mobile robot 20 autonomously moves toward the next passing point. In this way, the mobile robot 20 sequentially passes the passing points so as to arrive at the transport destination. Further, the mobile robot 20 may estimate its position and transmit a signal indicating that the mobile robot 20 has passed the passing point to the host management device 10. Thus, the host management device 10 can manage the current position and the transport status of each mobile robot 20.

Similar to the detection unit 116, the detection unit 216 detects that the transport destination of the transported object is different from the receiving location. The process of the detection unit 116 will be described later. In the following description, it is assumed that the detection unit 216 of the mobile robot 20 mainly performs the detection process independently, but the detection unit 116 of the host management device 10 may perform the detection process. Alternatively, the detection unit 116 and the detection unit 216 may cooperate to perform the detection process or share the detection process. Further, at least one of the detection unit 116 and the detection unit 216 does not have to be provided.

The storage unit 22 stores a floor map 221, a robot control parameter 222, and transported object information 226. FIG. 2 shows only a part of the information stored in the storage unit 22, and the storage unit 22 also includes information other than the floor map 221, the robot control parameter 222, and the transported object information 226 shown in FIG. 2. The floor map 221 is map information of a facility in which the mobile robot 20 moves. The floor map 221 is, for example, an item obtained by downloading the floor map 121 of the host management device 10. The floor map 221 may be created in advance. Further, the floor map 221 may not be the map information of the entire facility but may be the map information including a part of the area in which the mobile robot 20 is planned to move.

The robot control parameter 222 is a parameter for operating the mobile robot 20. The robot control parameter 222 includes, for example, a distance threshold value from a peripheral object. The robot control parameter 222 also includes a speed upper limit value of the mobile robot 20.

Similar to the transported object information 126, the transported object information 226 includes information on the transported object. The transported object information 226 includes information such as the content (type) of the transported object, the transport source, and the transport destination. The transported object information 226 may include information indicating the status such as transport under way, pre-transport (before loading), and post-transport. The transported object information 226 is associated with these types of information for each transported object. The transported object information 126 will be described later. The transported object information 226 only needs to include information on the transported object transported by the mobile robot 20. Therefore, the transported object information 226 is a part of the transported object information 126. That is, the transported object information 226 does not have to include the information on the transport performed by other mobile robots 20.

The drive control unit 212 refers to the robot control parameter 222 and stops or decelerates the operation in response to the fact that the distance indicated by the distance information obtained from the distance sensor group 24 has fallen below the distance threshold value. The drive control unit 212 controls the drive unit 26 so that the mobile robot 20 travels at a speed equal to or lower than the speed upper limit value. The drive control unit 212 limits the rotation speed of the drive wheels so that the mobile robot 20 does not move at a speed equal to or higher than the speed upper limit value.

Configuration of Mobile Robot 20

Figure 3:
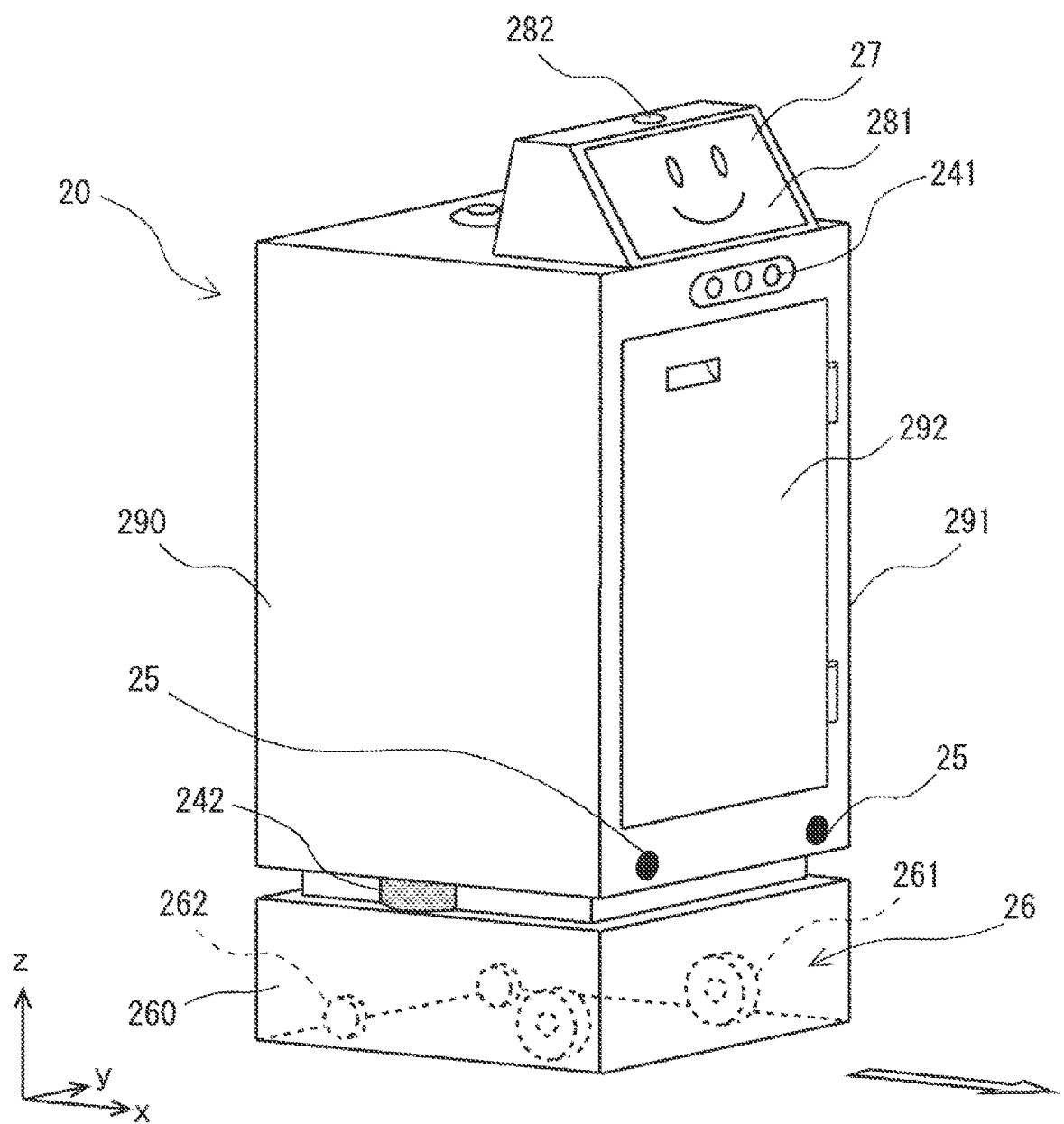
FIG. 3 is a schematic view showing an example of the mobile robot.

Here, the appearance of the mobile robot 20 will be described. FIG. 3 shows a schematic view of the mobile robot 20. The mobile robot 20 shown in FIG. 3 is one of the modes of the mobile robot 20, and may be in another form. In FIG. 3, the x direction is the forward and backward directions of the mobile robot 20, the y direction is the right-left direction of the mobile robot 20, and the z direction is the height direction of the mobile robot 20.

The mobile robot 20 includes a main body portion 290 and a carriage portion 260. The main body portion 290 is installed on the carriage portion 260. The main body portion 290 and the carriage portion 260 each have a rectangular parallelepiped housing, and each component is installed inside the housing. For example, the drive unit 26 is housed inside the carriage portion 260.

The main body portion 290 is provided with the storage 291 that serves as a storage space and a door 292 that seals the storage 291. The storage 291 is provided with a plurality of shelves, and the availability is managed for each shelf. For example, by providing various sensors such as a weight sensor in each shelf, the availability can be updated. The mobile robot 20 moves autonomously to transport the transported object stored in the storage 291 to the destination instructed by the host management device 10. The main body portion 290 may include a control box or the like (not shown) in the housing. Further, the door 292 may be able to be locked with an electronic key or the like. Upon arriving at the transport destination, the user U2 unlocks the door 292 with the electronic key. Alternatively, the door 292 may be automatically unlocked when the mobile robot 20 arrives at the transport destination.

As shown in FIG. 3, front-rear distance sensors 241 and right-left distance sensors 242 are provided as the distance sensor group 24 on the exterior of the mobile robot 20. The mobile robot 20 measures the distance of the peripheral objects in the front-rear direction of the mobile robot 20 by the front-rear distance sensors 241. The mobile robot 20 measures the distance of the peripheral objects in the right-left direction of the mobile robot 20 by the right-left distance sensors 242.

For example, the front-rear distance sensor 241 is provided on the front surface and the rear surface of the housing of the main body portion 290. The right-left distance sensor 242 is provided on the left side surface and the right side surface of the housing of the main body portion 290. The front-rear distance sensors 241 and the right-left distance sensors 242 are, for example, ultrasonic distance sensors and laser rangefinders. The front-rear distance sensors 241 and the right-left distance sensors 242 detect the distance from the peripheral objects. When the distance from the peripheral object detected by the front-rear distance sensor 241 or the right-left distance sensor 242 is equal to or less than the distance threshold value, the mobile robot 20 decelerates or stops.

The drive unit 26 is provided with drive wheels 261 and casters 262. The drive wheels 261 are wheels for moving the mobile robot 20 frontward, rearward, rightward, and leftward. The casters 262 are driven wheels that roll following the drive wheels 261 without being given a driving force. The drive unit 26 has a drive motor (not shown) and drives the drive wheels 261.

For example, the drive unit 26 supports, in the housing, two drive wheels 261 and two casters 262, each of which are in contact with the traveling surface. The two drive wheels 261 are arranged so that their rotation axes coincide with each other. Each drive wheel 261 is independently rotationally driven by a motor (not shown). The drive wheels 261 rotate according to a control command value from the drive control unit 212 of FIG. 2. The casters 262 are driven wheels that are provided so that a pivot axis extending in the vertical direction from the drive unit 26 supports the wheels at a position away from the rotation axis of the wheels, and thus follow the movement direction of the drive unit 26.

For example, when the two drive wheels 261 are rotated in the same direction at the same rotation speed, the mobile robot 20 travels straight, and when the two drive wheels 261 are rotated at the same rotation speed in the opposite directions, the mobile robot 20 pivots around the vertical axis extending through approximately the center of the two drive wheels 261. Further, by rotating the two drive wheels 261 in the same direction and at different rotation speeds, the mobile robot 20 can proceed while turning right and left. For example, by making the rotation speed of the left drive wheel 261 higher than the rotation speed of the right drive wheel 261, the mobile robot 20 can make a right turn. In contrast, by making the rotation speed of the right drive wheel 261 higher than the rotation speed of the left drive wheel 261, the mobile robot 20 can make a left turn. That is, the mobile robot 20 can travel straight, pivot, turn right and left, etc. in any direction by controlling the rotation direction and the rotation speed of each of the two drive wheels 261.

Further, in the mobile robot 20, the display unit 27 and an operation interface 281 are provided on the upper surface of the main body portion 290. The operation interface 281 is displayed on the display unit 27. When the user touch-operates the operation interface 281 displayed on the display unit 27, the operation reception unit 28 can receive an instruction input from the user. An emergency stop button 282 is provided on the upper surface of the display unit 27. The emergency stop button 282 and the operation interface 281 function as the operation reception unit 28.

The display unit 27 is, for example, a liquid crystal panel, which displays a character's face as an illustration or presents information on the mobile robot 20 in text or with an icon. By displaying a character's face on the display unit 27, it is possible to give surrounding observers the impression that the display unit 27 is a pseudo face portion. It is also possible to use the display unit 27 or the like installed in the mobile robot 20 as the user terminal 400.

The cameras 25 are installed on the front surface of the main body portion 290. Here, the two cameras 25 function as stereo cameras. That is, the two cameras 25 having the same angle of view are provided so as to be horizontally separated from each other. An image captured by each camera 25 is output as image data. It is possible to calculate the distance from the subject and the size of the subject based on the image data of the two cameras 25. The arithmetic processing unit 21 can detect a person, an obstacle, or the like at positions forward in the movement direction by analyzing the images of the cameras 25. When there are people or obstacles at positions forward in the traveling direction, the mobile robot 20 moves along the route while avoiding the people or the obstacles. The image data of the cameras 25 is transmitted to the host management device 10.

The mobile robot 20 recognizes the peripheral objects and identifies the position of the mobile robot 20 itself by analyzing the image data output by the cameras 25 and the detection signals output by the front-rear distance sensors 241 and the right-left distance sensors 242. The cameras 25 capture images of the front of the mobile robot 20 in the traveling direction. As shown in FIG. 3, the mobile robot 20 considers the side on which the cameras 25 are installed as the front of the mobile robot 20. That is, during normal movement, the traveling direction is the forward direction of the mobile robot 20 as shown by the arrow.

Transported Object Information

The transported object information 126 will be described with reference to FIG. 4. FIG. 4 is a table showing an example of the transported object information 126. The transported object information 126 includes the content of the transported object, the transport source, the transport destination, the planned user, the robot ID in charge of the transport, and the status. These types of information are associated with each transported object. The content of the transported object is information indicating the type of the transported object. For example, medicines, equipment, specimens, etc. are input. The transport source indicates the location where the mobile robot 20 loads the transported object. The transport destination indicates the delivery destination of the transported object.

The planned user indicates the person who uses the transported object. For example, the planned user indicates the name or ID of a patient. Alternatively, the planned user may indicate the name and ID of a staff member such as a nurse or a doctor. Needless to say, the planned user may include information on both the patient and the staff member. The content, the transport source, the transport destination, and the planned user can be set based on the transport request information.

The robot ID is the ID of the mobile robot 20 in charge of transporting the transported object. The robot ID is set based on the route plan. The status is information indicating whether it is before, during, or after transport of the transported object. The status is updated when the mobile robot 20 loads the transported object and when the receipt of the transported object is completed.

The transported object information 126 is transmitted to the respective mobile robots 20 in charge of transporting the transported object. For example, the transported object information 226 of the mobile robot 20 includes information on the transported object that the mobile robot 20 is in charge of transporting. That is, the transported object information of the transported object for the robot ID "BBB" does not have to be transmitted to the mobile robot 20 having the robot ID "AAA".

Figure 5:
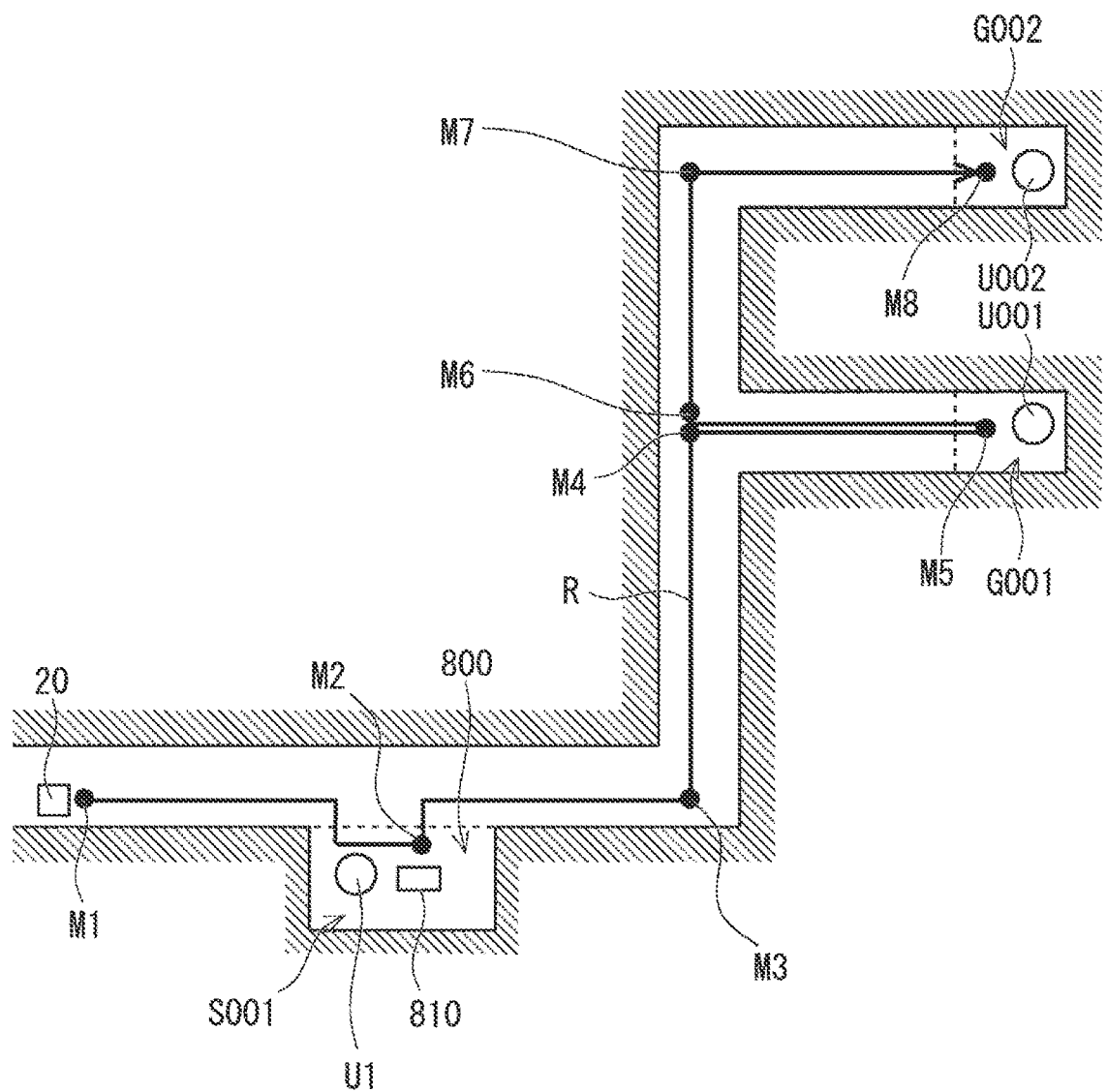
FIG. 5 is a diagram showing an example of a movement route of the mobile robot.

The transport of the transported objects of "001" and "002" in FIG. 4 will be described with reference to FIG. 5. Here, the two transported objects are loaded on one mobile robot 20 at the same transport source S001. In this case, the transport source S001 of the two transported objects is a dispensing room 800. The dispensing room 800 is provided with the dispensing machine 810 shown in FIG. 1. The user U1, who is a pharmacist, makes a transport request for the two transported objects.

Since each of the two medicines are administered to different planned users U001 and U002, the mobile robot 20 moves from the transport source S001 to different transport destinations G001 and G002 in this order. After the mobile robot 20 receives the two transported objects at the transport source S001, the mobile robot 20 moves in the order of the transport destination G001 and the transport destination G002. That is, the mobile robot 20 moves from the transport source S001 to the transport destination G002 via the transport destination G001. The route planning unit 115 sets passing points M1 to M8 in response to the transport requests. Therefore, the route search is performed so that the mobile robot 20 moves in the order of the passing points M1, M2, M3, M4, M5, M6, M7, and M8. The mobile robot 20 moves along a route R.

First, the mobile robot 20 moves from the passing point M1 to the passing point M2. The passing point M2 is a point in the dispensing room 800. The user U1 stores the two transported objects in the storage 291 of the mobile robot 20. Here, the transport destination of one transported object is the transport destination G001, and the transport destination of the other transported object is the transport destination G002.

The transport destination G001 and the transport destination G002 are the receiving locations where the recipients of the transported objects are present. The planned user U001 who is the recipient is present at the transport destination G001. The planned user U002 who is the recipient is present at the transport destination G002. The recipient may be a staff member such as a nurse or may be a patient. At the transport destination G001, the planned user U001 needs to receive only one of the two transported objects. When the door 292 shown in FIG. 3 is unlocked at the receiving location, the planned user U001 may take out the wrong transported object. For example, the planned user U001 may take out the transported object of "002" at the transport destination G001 that is the receiving location.

In the present embodiment, the detection unit 216 of the mobile robot 20 that transports a plurality of transported objects detects whether the transport destination of the transported object is different from the receiving location. That is, the detection unit 216 determines whether the receiving location (current position) and the transport destination match for each transported object. The mobile robot 20 or the user terminal 400 performs output according to the detection result of the detection unit 216. When the receiving location and the transport destination are different, information indicating that there is a transported object having a different transport destination is output to the planned user U001 who is the recipient.

For example, the display unit 27 outputs a warning message such as "Please take out only the transported object [001]", "Please do not take out the transported object [002]", and "Please be careful not to take out the wrong luggage." The output may be a display output by the display unit 27, or may be an audio output by a speaker or the like. Further, performing the output is not limited to the display unit 27, and the user terminal 400 may perform the output.

By performing the output by the display unit 27 or the like according to the detection result, it is possible to suppress the recipient from erroneously taking out the transported object of a different transport destination. This enables appropriate transport, and transport efficiency can be improved. Further, performing the output according to the detection result eliminates the need to provide the storage 291 and the door 292 for each of the transported objects having different transport destinations. Since a plurality of transported objects can be stored in one storage 291 provided with one door 292, the manufacturing cost of the mobile robot 20 can be suppressed.

The detection unit 216 can perform the detection process by comparing the current position with the transport destination of the transported object information 226 for each transported object. The detection unit 216 may perform the detection process only during the transport of a plurality of transported objects. Further, the detection unit 216 can perform the detection when a transported object having a different transport destination is newly stored. The detection process by the detection unit 216 may be performed at the time of arrival at the receiving location of each transported object, or may be performed before arrival.

Alternatively, the detection unit 116 of the host management device 10 can perform the detection process by comparing the current position with the transport destination of the transported object information 126 for each transported object. The host management device 10 transmits a control signal to the mobile robot 20 having the transport destination that is different from the receiving location. Thus, the mobile robot 20 can notify the recipient of the detection result. Needless to say, the host management device 10 may transmit the detection result to the user terminal 400 of the user instead of the mobile robot 20.

Cooperation with Electronic Medical Record System 700

Further, in the present embodiment, the host management device 10 may perform the detection process in cooperation with the electronic medical record system 700 shown in FIG. 1. For example, in the electronic medical record system 700, patient information on patients is created and registered. The patient information includes, for example, location information indicating the location of the patient. For example, the location information indicates a hospital room of an inpatient or a clinical department where the patient receives medical treatment. For example, when the patient's condition suddenly changes, or when a new diagnosis is made by an examination, a doctor or the like inputs the location movement of the patient to the electronic medical record system 700 via the user terminal 400.

Figure 6:
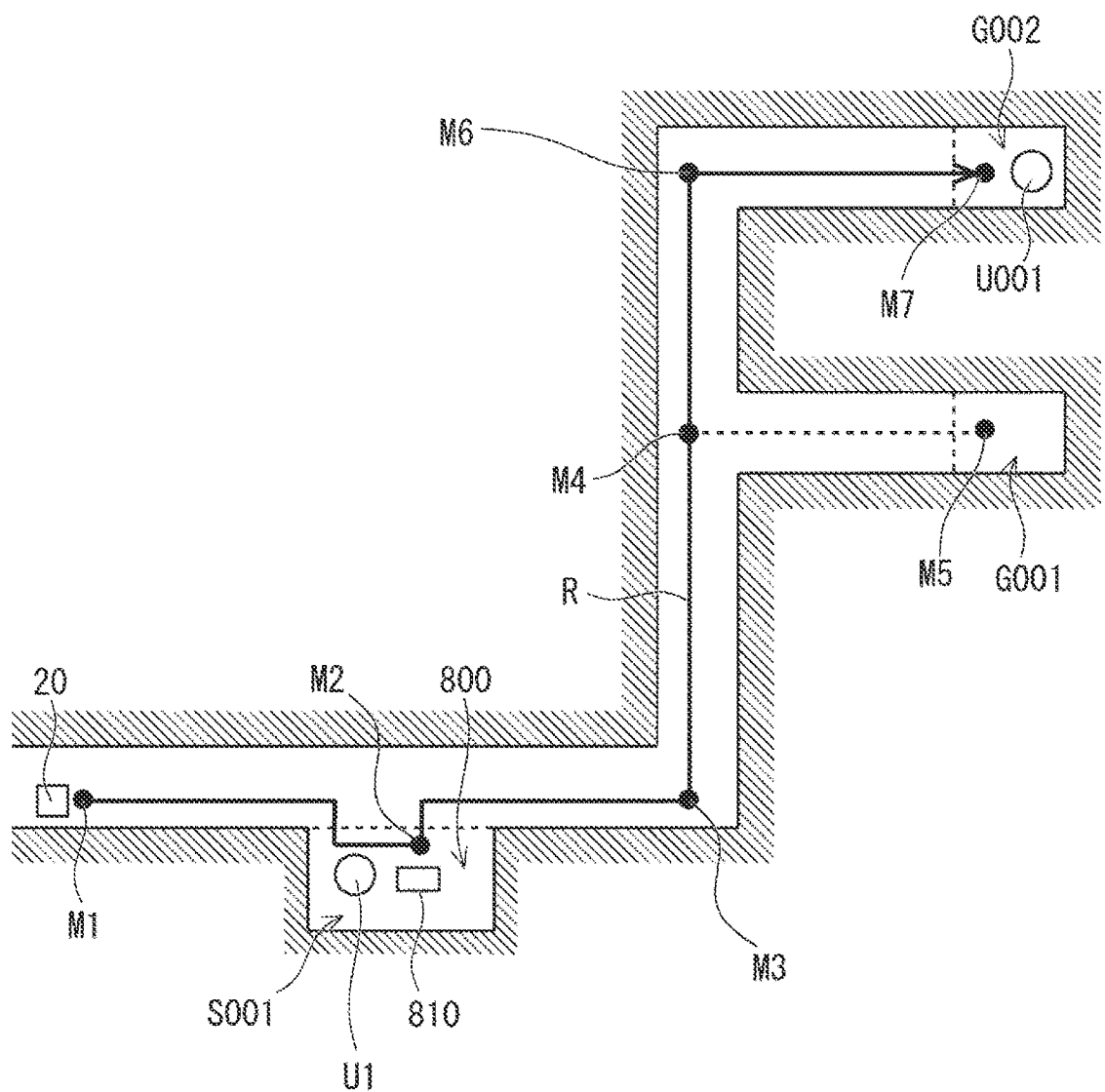
FIG. 6 is a diagram showing another example of the movement route of the mobile robot.

Here, a case where the medicine dispensed in the dispensing room 800 is transported to the patient is considered. FIG. 6 is a diagram showing an example in which the mobile robot 20 moves with the dispensing room 800 as the transport source S001. At the estimated completion time for completing the dispensing, the mobile robot 20 goes to the transport source S001 to pick up the medicine. For example, the route planning unit 115 performs route planning to deliver the medicine that has been prescribed in the morning examination to the patient in the evening.

There is a case where the location of the planned user U001 who is the patient has moved before the mobile robot 20 moves to the transport destination of the medicine. For example, the hospital room of the inpatient may change. Alternatively, the patient may move to another clinical department. Information on the location movement of the patient is input to the electronic medical record system 700. For example, a doctor or the like uses the user terminal 400 to input information on the location movement of the patient. Here, the hospital room of the planned user U001 who takes the medicine has moved from the transport destination G001 to the transport destination G002.

When a doctor or the like inputs information on the location movement of the patient to the electronic medical record system 700, the electronic medical record system 700 transmits the information on the location movement to the host management device 10. The host management device 10 updates the information on the location where the patient is present. The host management device 10 detects that the transport destination is different from the receiving location based on the updated information.

For example, when the host management device 10 acquires the information on the location movement of the planned user U001 from the electronic medical record system 700, the host management device 10 searches the transported object information 126 for the transported object of the planned user U001. When the route planning has already been performed for the transported object of the planned user U001, the detection unit 116 detects that the transport destination and the receiving location are different. The host management device 10 transmits the detection result to the mobile robot 20 that transports the transported object of the planned user U001 and the user terminal 400 located at the receiving location. The mobile robot 20 or the user terminal 400 outputs the detection result.

In this way, when the host management device 10 acquires the information on the location movement of the planned user U001 from the electronic medical record system 700, the host management device 10 updates the transported object information 126. Then, the detection unit 116 performs the detection process with reference to the updated transported object information 126. Thus, the detection process is performed based on the latest information, so that the detection accuracy can be improved.

Further, when the detection unit 216 detects that the transport destination is different from the receiving location, the mobile robot 20 may transport the transported object to the correct transport destination. As described above, when the location information of the planned user U001 is updated, the arithmetic processing unit 21 updates the transport destination of the transported object information 126 with the updated location information. In FIG. 6, the planned user U001 has moved from the transport destination G001 to the transport destination G002. Thus, in the transported object information 126, the transport destination of the transported object is updated to the transport destination G002.

The route planning unit 115 performs route planning with the updated transport destination G002 as the correct transport destination. For example, in FIG. 6, before the update of the transport destination, the passing points M1 to M5 to the transport destination G001 before the update are set. When the transport destination is updated to the transport destination G002, the route planning unit 115 deletes the passing point M5 from the route planning information 125 of the mobile robot 20. The route planning unit 115 adds the passing points M6 and M7 to the route planning information 125 of the mobile robot 20. Although the mobile robot 20 was scheduled to move in the order of the passing points M1, M2, M3, M4, and M5, due to the route update, the mobile robot 20 moves in the order of the passing points M1, M2, M3, M4, M6, and M7.

Further, the host management device 10 transmits the updated transported object information to the mobile robot 20. The mobile robot 20 re-searches the route R with the updated transport destination as the correct transport destination. Thus, the mobile robot 20 does not stop at the transport destination G001, which was the transport destination before the update, but transports the transported object to the transport destination G002, which is the transport destination after the update. That is, since the mobile robot 20 does not move to the passing point M5, the moving distance is shortened. This enables transportation with higher efficiency.

Cooperation with Dispensing Machine 810

Further, in the present embodiment, the mobile robot 20 may execute the transport task in cooperation with the dispensing machine 810 shown in FIG. 1. Specifically, the host management device 10 acquires, from the dispensing machine 810, the estimated dispensing time for completing the dispensing of the medicine that is the transported object. Then, the route planning unit 115 performs route planning so that the mobile robot 20 picks up the transported object according to the estimated dispensing time. As a result, the mobile robot 20 can go to the transport source S001 where the dispensing machine 810 is located to pick up the transported object immediately before or after the estimated dispensing time. This enables highly efficient transportation.

Specifically, the user U1 who is a pharmacist operates the dispensing machine 810 or the user terminal 400 to input the estimated dispensing time. Alternatively, the dispensing machine 810 may determine the estimated dispensing time based on the dispensing content and the like. The estimated dispensing time may be stored as the transported object information 126, 226. Further, the user U1 inputs the name and the like of the patient who is the planned user U001. Thus, the mobile robot 20 goes to pick up the medicine according to the estimated dispensing time. For example, the mobile robot 20 moves to the dispensing room or the dispensing machine immediately after the estimated dispensing time. Then, the user U1 loads the medicine on the mobile robot 20. Thus, the medicine can be transported efficiently.

IC Tag

Further, the detection unit 216 may detect that the transport destination is different from the receiving location based on an IC tag attached to the transported object. For example, the IC tag may include information on a patient or a staff member who uses the medicine that is the transported object. The detection unit 216 performs the detection process based on the information included in the IC tag. The detection unit 216 and the user terminal 400 may have an IC tag reader that reads the information of the IC tag.

The detection unit 116 or the detection unit 216 detects that the transport destination according to the information stored in the IC tag and the receiving location are different. For example, the planned recipient reads the information of the IC tag using the IC tag reader. The detection unit 216 performs the detection process by comparing the current position with the transport destination based on the information of the IC tag. Then, the display unit 27 performs the display according to the detection result. This enables appropriate transport.

Transport Method

Figure 7:
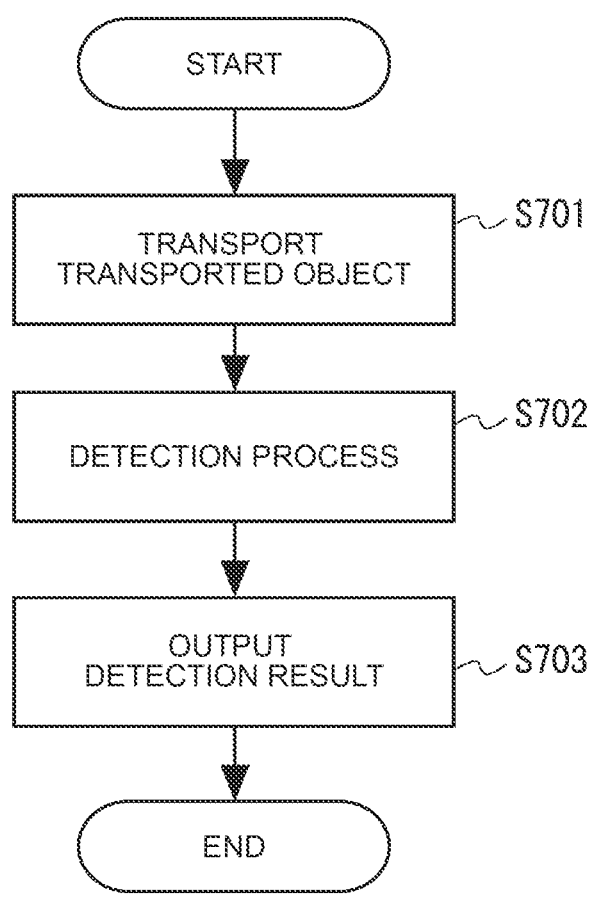
FIG. 7 is a flowchart showing a transport method according to the present embodiment.

FIG. 7 is a flowchart showing a control method according to the present embodiment. FIG. 7 shows the processing after the route planning is performed in response to the transport request. That is, FIG. 7 shows a process in which the mobile robot 20 is moving along the route transmitted from the host management device 10.

First, the mobile robot 20 transports the transported object (S701). Here, the mobile robot 20 loads two or more transported objects to execute the transport task. Next, the detection unit 116 performs the detection process (S702). As described above, the detection unit 116 detects that the transport destination is different from the receiving location based on various types of information. Alternatively, the detection unit 216 may perform the detection process.

Then, the mobile robot 20 or the user terminal 400 outputs the detection result (S703). Thus, information that there is a transported object of a different transport destination is output to the recipient at the receiving location. It is possible to suppress the recipient from erroneously taking out the transported object of a different transport destination. This enables appropriate transport.

A part or all of the processing in the host management device 10, the mobile robot 20, or the like described above can be realized as a computer program. Such a program can be stored using various types of non-transitory computer-readable media and supplied to a computer. The non-transitory computer-readable media include various types of tangible recording media. Examples of the non-transitory computer-readable media include magnetic recording media (e.g. flexible disks, magnetic tapes, hard disk drives), magneto-optical recording media (e.g. magneto-optical disks), compact disc read-only memory (CD-ROM), compact disc recordable (CD-R), compact disc rewritable (CD-R/W), and semiconductor memory (e.g. mask ROM, programmable ROM (PROM), erasable PROM (EPROM), flash ROM, random access memory (RAM)). The program may also be supplied to the computer by various types of transitory computer-readable media. Examples of the transitory computer-readable media include electrical signals, optical signals, and electromagnetic waves. The transitory computer-readable media can supply the program to the computer via a wired communication path such as an electric wire and an optical fiber, or a wireless communication path.

The present disclosure is not limited to the above embodiment, and can be appropriately modified without departing from the spirit. For example, in the above embodiment, a system in which a transport robot autonomously moves in a hospital has been described, but the above-described system can transport a predetermined article in a hotel, a restaurant, an office building, an event venue, or a complex facility as luggage.

What is claimed is:

1. A transport system for transporting a transported object using a mobile robot that is autonomously moveable, wherein:
   the mobile robot transports a plurality of transported objects;
   a first user terminal of a first user transmits a transport request to a server, the transport request including a content of a transported object, a transport source of the transported object, a transport destination of the transported object, an estimated arrival time at the transport source, and an estimated arrival time at the transport destination;
   the server transmits an operation command to the mobile robot to cause the mobile robot to go to the transport source to pick up the transported object;
   after the mobile robot receives the transported object at the transport source, the mobile robot transmits a signal to a second user terminal of a second user at the transport destination, and autonomously moves to the transport destination;
   the server determines a congestion status by estimating a number of mobile robots and a number of people at a first estimated time when the mobile robot passes through a first location;
   the server determines a movement route from the transport source to the transport destination including one or more passing points based on the congestion status; and
   when information on a location movement of a patient is input to an electronic medical record system that stores patient information, the transport system detects that the transport destination is different from the receiving location based on the information on the location movement.

2. The transport system according to claim 1, wherein the transport system detects that the transport destination is different from the receiving location based on an IC tag attached to the transported object.

3. The transport system according to claim 1, wherein when the transport system acquires an estimated dispensing time for completing dispensing of medicine that is the transported object, the mobile robot goes to pick up the medicine according to the estimated dispensing time.

4. The transport system according to claim 1, wherein upon detecting that the transport destination is different from the receiving location, the transport system transports the transported object to a correct transport destination.

5. A transport method for transporting a transported object using a mobile robot that is autonomously moveable, the transport method comprising:

transporting a plurality of the transported objects by the mobile robot;

transmitting, by a first user terminal of a first user, a transport request to a server, the transport request including a content of a transported object, a transport source of the transported object, a transport destination of the transported object, an estimated arrival time at the transport source, and an estimated arrival time at the transport destination;

transmitting, by the server, an operation command to the mobile robot to cause the mobile robot to go to the transport source to pick up the transported object;

after the mobile robot receives the transported object at the transport source, transmitting, by the mobile robot, a signal to a second user terminal of a second user at the transport destination, and autonomously moving the mobile robot to the transport destination;

determining a congestion status by estimating a number of mobile robots and a number of people at a first estimated time when the mobile robot passes through a first location;

determining a movement route from the transport source to the transport destination including one or more passing points based on the congestion status; and detecting, when information on a location movement of a patient is input to an electronic medical record system that stores patient information, that the transport destination is different from the receiving location based on the information on the location movement.

6. The transport method according to claim 5, further comprising detecting that the transport destination is different from the receiving location based on an IC tag attached to the transported object.

7. The transport method according to claim 5, further comprising going to pick up medicine according to an estimated dispensing time by the mobile robot, when the estimated dispensing time for completing dispensing of the medicine that is the transported object is acquired.

8. The transport method according to claim 5, further comprising transporting the transported object to a correct transport destination upon detecting that the transport destination is different from the receiving location.

9. A non-transitory storage medium storing a program that causes a computer to execute a transport method for transporting a transported object using a mobile robot that is autonomously moveable, wherein the transport method includes:

transporting a plurality of the transported objects by the mobile robot;

transmitting, by a first user terminal of a first user, a transport request to a server, the transport request including a content of a transported object, a transport source of the transported object, a transport destination of the transported object, an estimated arrival time at the transport source, and an estimated arrival time at the transport destination;

transmitting, by the server, an operation command to the mobile robot to cause the mobile robot to go to the transport source to pick up the transported object;

after the mobile robot receives the transported object at the transport source, transmitting, by the mobile robot, a signal to a second user terminal of a second user at the transport destination, and autonomously moving to the transport destination;

determining, by the server, a congestion status by estimating a number of mobile robots and a number of people at a first estimated time when the mobile robot passes through a first location; and determining, by the server, a movement route from the transport source to the transport destination including one or more passing points based on the congestion status;

wherein when information on a location movement of a patient is input to an electronic medical record system that stores patient information, the program detects that the transport destination is different from the receiving location based on the information on the location movement.

10. The non-transitory storage medium according to claim 9, wherein the program detects that the transport destination is different from the receiving location based on an IC tag attached to the transported object.

11. The non-transitory storage medium according to claim 9, wherein when an estimated dispensing time for completing dispensing of medicine that is the transported object is acquired, the mobile robot goes to pick up the medicine at the estimated dispensing time.

12. The non-transitory storage medium according to claim 9, wherein upon detecting that the transport destination is different from the receiving location, the program transports the transported object to a correct transport destination.

13. The transport system according to claim 1, wherein the transported object is a medicine.

14. The transport system according to claim 1, wherein the server determines the transport destination by accessing an electronic medical record system.

15. The transport system according to claim 1, wherein the server determines the estimated arrival time at the transport destination based on an estimated dispensing time of a dispensing machine.

* * * * *